(12) United States Patent
Pisano et al.

(10) Patent No.: US 7,589,099 B2
(45) Date of Patent: Sep. 15, 2009

(54) 7-T-BUTOXYIMINOMETHYLCAMPTOTHECIN CONJUGATED IN POSITION 20 WITH INTEGRIN ANTAGONISTS

(75) Inventors: Claudio Pisano, Rome (IT); Giuseppe Giannini, Pomezia (IT); Loredana Vesci, Pomezia (IT); Domenico Alloatti, Pomezia (IT); Sergio Penco, Milan (IT); Alma Dal Pozzo, Milan (IT); Ni Ming Hong, Milan (IT); Sabrina Dallavalle, Vimercate (IT); Lucio Merlini, Milan (IT); Maria Ornella Tinti, Pomezia (IT); Franco Zunino, Milan (IT)

(73) Assignee: Sigma-Tau Industrie Farmaceutiche Reunite S.p.A., Rome (IT)

( * ) Notice: Subject to any disclaimer, the term of this patent is extended or adjusted under 35 U.S.C. 154(b) by 100 days.

(21) Appl. No.: 11/596,016

(22) PCT Filed: Apr. 28, 2005

(86) PCT No.: PCT/IT2005/000245

§ 371 (c)(1),
(2), (4) Date: Nov. 9, 2006

(87) PCT Pub. No.: WO2005/110486

PCT Pub. Date: Nov. 24, 2005

(65) Prior Publication Data

US 2007/0225311 A1      Sep. 27, 2007

(30) Foreign Application Priority Data

May 13, 2004 (IT) .......................... RM2004A0242

(51) Int. Cl.
  A61K 31/4745   (2006.01)
  C07D 491/22    (2006.01)
(52) U.S. Cl. ........................................ 514/283; 546/48
(58) Field of Classification Search ................. 514/283; 546/48

See application file for complete search history.

(56) References Cited

FOREIGN PATENT DOCUMENTS

WO    WO 03/101996    * 12/2003

OTHER PUBLICATIONS

Erdreich-Epstein A. et al, (Cancer Research, 2000, 60, 712).
Uhm J.H. et al. (Clin. Cancer Res., 1999, 5, 1587).
Yaeger T.E., et al., Clinical Oncology, 159, 2001.
Rader C., et al. , Faseb J., 2002;16,2000.
Mizejewski G.J., Exp. Biol. Med., 1999, 222, 124.
Li et al, "Three inhibitors of type 1 human immunodeficiency virus long . . . ", Proc. Natl. Acad. Sci. USA, vol. 90, pp. 1839-1842, Mar. 1993.
Proulx et al, "Treatment of Visceral Leishmaniasis with Sterically . . . ", Antimicrobial Agents and Chemotherapy, Sep. 2001, vol. 45, No. 9, p. 2623-2627.
Garcia-Carbonero et al, "Current Perspectives on the Clinical Experience, Pharmacology, and Continued Development of the Camptothecins", Clinical Cancer Research, vol. 8, 641-661, Mar. 2002.

* cited by examiner

*Primary Examiner*—Charanjit S Aulakh
(74) *Attorney, Agent, or Firm*—Lucas & Mercanti, LLP

(57) ABSTRACT

Compounds of Formula (I) are described:

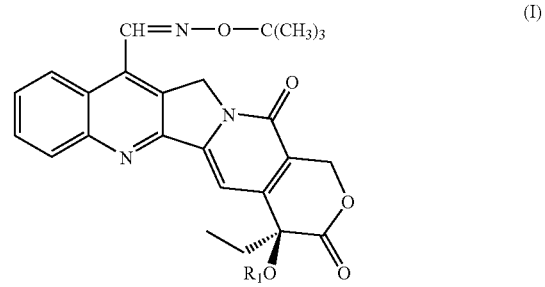

in which the $R_1$ group is as defined in the specification and includes the condensation of 7-t-butoxyiminomethylcamptothecin in position 20 with a cyclopeptide containing the RGD sequence. Said compounds are endowed both with high affinity for integrin receptors $\alpha_v\beta_3$ and $\alpha_v\beta_5$ and with selective cytotoxic activity on human tumour cell lines at micromolar concentrations.

9 Claims, No Drawings

7-T-BUTOXYIMINOMETHYLCAMPTOTHECIN CONJUGATED IN POSITION 20 WITH INTEGRIN ANTAGONISTS

This application is the US national phase of international application PCT/IT2005/000245, filed 28 Apr. 2005, which designated the U.S. and claims priorityof IT RM2004A000242, filed 13 May 2004, the entire contents of each of which arehereby incorporated by reference.

FIELD OF THE INVENTION

The present invention relates to compounds with cytotoxic activity consisting of cyclopeptides containing the RGD sequence and derivatives of camptothecin, methods for the preparation thereof, their use as medicaments and compositions containing them.

In particular, the compounds described in the present invention are endowed with both high affinity for integrins $\alpha_v\beta_3$ and $\alpha_v\beta_5$ and selective cytotoxic activity on human cell lines at micromolar concentrations.

BACKGROUND TO THE INVENTION

Chemotherapeutic anticancer agents are the drugs with the most restrictive therapeutic window. In fact, since their cytotoxic activity is non-selective they may indiscriminately damage all the cells of the body with which they come into contact.

There currently exists the problem of directing the cytotoxic agent selectively against the tumour cells, allowing the agent to exert its activity without damaging the cells of the healthy surrounding tissues, or at least limiting the damage as much as possible.

It has been reported in the literature that blocking the integrins $\alpha_v\beta_3$ and $\alpha_v\beta_5$ by means of the use of selective cyclopeptides, the reference compound for which is regarded as cyclopentapeptide c(Arg-Gly-Asp-D-Phe-Val) (*JACS* 1997, 119, 1328-35; international patent application WO 97/06791), or by means of the use of monoclonal antibodies (*Cell*, 1994, 79, 1157-64) leads to the blocking of angiogenesis and to a reduction of tumour growth. In addition, anti-metastatic effects have also been observed (*J. Clin. Invest.*, 1995, 96, 1815). Brooks et al. (*Science*, 1994, 264, 569-71) reported that the endo-thelial cells of the tumour vasculature and the tumour cells themselves preferentially express integrin $\alpha_v\beta_3$ compared to the quiescent cells of normal tissue. Among the compounds at an advanced stage of clinical development, we may mention c(Arg-Gly-Asp-D-Phe-MeVal), or EMD121974 or cilengitide.

Ruoslati and co-workers (*Current Opinion in Oncology*, 1998, 10, 560-5) showed that RGD analogues that bind to the tumour endothelium, once conjugated to the cytotoxic agent doxorubicin, form compounds that are more efficient and less toxic than doxorubicin alone. These authors also demonstrated, beyond any reasonable doubt, that the effect is attributable to the conjugation to RGD, inasmuch as the binding is antagonised by the free peptide itself (*Arap, Pasqualini and Ruoslati, Science*, 1998, 279, 377-380). Later, the same authors carried out other experiments consisting in chemically binding a pro-apoptotic peptide sequence to an RGD analogue, demonstrating that the new compounds were selectively toxic for angiogenic endothelial cells and had anticancer activity in mice (*Ruoslati, Nature Medicine*, 1999, 5, 1032-8).

Marcus et al., in international patent application WO 01/17563, describe specific anticancer activity for cytotoxic agents, such as camptothecin, conjugated by means of a spacer, consisting of one or more amino acids, to a non-peptidic inhibitor antagonist of integrins $\alpha_v\beta_3$ and $\alpha_v\beta_5$.

Aoki et al., *Cancer Gene Therapy*, 2001, 8, 783-787 describe the specific anticancer activity of a histidylated oligolysine conjugated to an RGD sequence, revealing a homing effect for tumours in mice.

The concept of binding at the cell surface mediated by integrins has been proposed for gene transport (Hart, et al., *J. Biol. Chem.*, 1994, 269, 12468-12474).

7-tert-butoxyiminomethylcamptothecin (or CPT184 or ST 1481 or Gimatecan) is a derivative of camptothecin which is active orally and is described in European Patent EP 1 044 977.

It has now been found that 7-t-butoxyiminomethylcamptothecin conjugated in position 20, possibly by means of suitable spacers, to cyclopeptide derivatives containing the RGD sequence yields compounds endowed with high, selective anticancer activity which can be advantageously used for the preparation of medicaments for the treatment of tumours.

By virtue of their selective cytotoxic activity on tumour cells, the compounds according to the present invention yield medicaments with fewer and less severe side effects.

DESCRIPTION OF THE INVENTION

The object of the present invention are derivatives of 7-t-butoxyiminomethylcamptothecin conjugated to cyclopeptide derivatives containing the RGD sequence. The resulting molecules possess unaltered both the cytotoxic properties of the original camptothecins and integrin binding properties with affinity comparable to that observed with the non-conjugated cyclopeptides. The result of this combination is to favour the concentration of the cytotoxic agent in those cells that most express integrins of the $\alpha_v\beta_3$ and $\alpha_v\beta_6$ type (homing). The cytotoxic agent exerts its intracellular activity in the conjugated and/or free form through enzymatic or hydrolytic action. The main object of the present invention are therefore compounds of Formula (I)

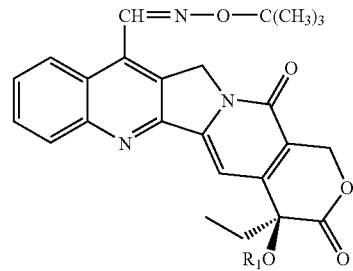

where:
$R_1$ is the U-X-Y group, in which:
U is either absent or one of the following groups —COCHR$_{10}$NH— or CON[(CH$_2$)$_{n2}$NHR$_7$]—CH$_2$—, where $R_{10}$ is H or is selected from the group consisting of: linear or branched $C_1$-$C_4$ alkyl, optionally substituted with $C_6$-$C_{14}$ aryl or an amino-alkyl $C_1$-$C_4$; $R_7$ is H or linear or branched $C_1$-$C_4$ alkyl; $n_2$ is an integer number from 2 to 6;
X is absent or is H or is a group selected among the following: —COCHR$_3$NH—, —COCHR$_6$(CH$_2$)$_{n3}$R$_4$—, —R$_4$—CH$_2$(OCH$_2$CH$_2$)$_{n4}$OCH$_2$R$_4$—, —R$_4$(Q)R$_4$—, —R$_5$[Arg-NH(CH$_2$)$_{n5}$CO]$_{n6}$R$_5$—, —R$_5$-[N-guanidinopropyl-Gly]$_{n6}$R$_5$—, in which $n_3$ is an integer number from 0 to 5, $n_4$ is an integer number from 0 to 50, $n_5$ is an integer number from 2 to 6, $n_6$ is an integer number from 2 to 7;

$R_3$ is H or linear or branched $C_1$-$C_4$ alkyl, optionally substituted with —COOH, —CONH$_2$, —NH$_2$ or —OH;

$R_4$ is selected from the group consisting of: —NH—, —CO—, —CONH—, —NHCO—;

$R_5$ is either absent or is the group —$R_4$(Q)$R_4$—;

$R_6$ is H or NH$_2$;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is absent or H or is the following group c(Arg-Gly-Asp-AA$_1$-AA$_2$), in which:

c means cyclic;

AA$_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-CF$_3$-Phe, (D)-4-acetylamino-Phe;

AA$_2$ is selected from the group consisting of: NW—CH[(CH$_2$)$_{n7}$—CO]—CO, NW—CH[(CH$_2$)$_{n7}$—NH]—CO, NW-[4-(CH$_2$)$_{n7}$—CO]-Phe, NW-[4-(CH$_2$)$_{n7}$—NH]-Phe, [NW]-Gly, NW-Val, in which W is selected from H, linear or branched $C_1$-$C_6$ alkyl, —(CH$_2$)$_{n7}$—COOH where $n_7$ is an integer number from 0 to 5, 4-carboxybenzyl, 4-aminomethylbenzyl;

with the proviso that X and Y cannot be both absent; the $N_1$-oxides, racemic mixtures, their single enantiomers, their single diastereoisomers, the forms E and Z, mixtures thereof, the pharmaceutically acceptable salts.

The present invention comprises the use of compounds with the above-mentioned compounds of Formula (I) as active ingredients for medicaments useful as topoisomerase I inhibitors. Among the therapeutic applications deriving from topoisomerase I inhibition, we mention parasitic or viral infections Given their particular pharmacological characteristics, the compounds of Formula (I) compounds are also useful for the preparation of medicaments for the treatment of tumours and the metastatic forms thereof.

The present invention also comprises pharmaceutical compositions containing compounds of Formula (I) as active ingredients, in mixtures with at least one pharmaceutically acceptable vehicle and/or excipient.

The compounds according to the present invention are the result of the condensation of 7-t-butoxyiminomethylcamptothecin, functionalised in position 20, with a cyclopeptide containing the Arg-Gly-Asp (RGD) sequence. This structural combination has the advantage of favouring the concentration of the cytotoxic agent (camptothecin) in the cells that most express integrins of the $\alpha_v\beta_3$ and $\alpha_v\beta_5$ type. The cytotoxic agent exerts its activity in the conjugated and/or free form through enzymatic or hydrolytic action.

The definitions of the various functional groups and residues, as well as the definitions of the pharmaceutically acceptable salts that figure in the above-mentioned formula (I), are common knowledge to any expert chemist and no particular definitions are necessary. However, reference to such groups can be found in the technical and patent literature, e.g. in international patent applications WO 00/53607, WO 03/101995 and WO 03/101996.

One initial group of preferred compounds consists of the compounds of Formula (I) where U and/or X are not absent.

The preferred compounds according to the present invention are the following:

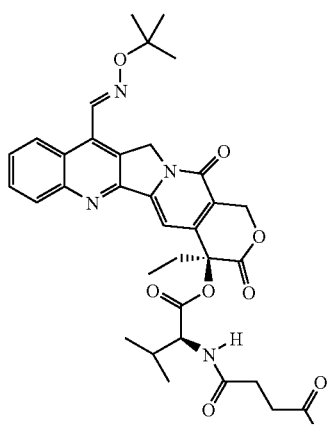

-continued

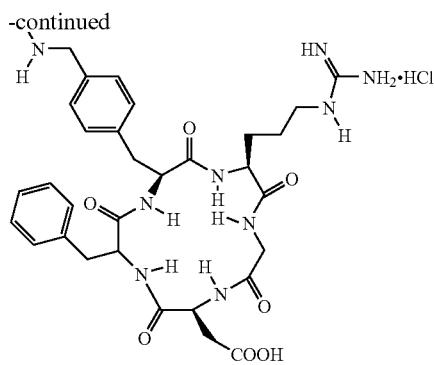
ST2670

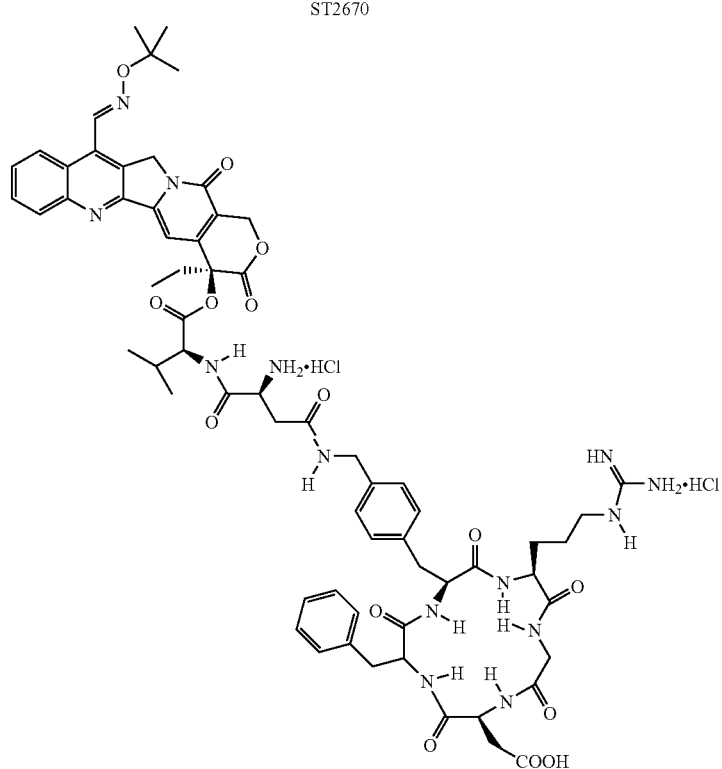
ST2671

Compounds of Formula (I) can be prepared with the process described here below and exemplified for the preferred compounds according to the invention. This process constitutes a further object of the invention.

Fundamentally, the compounds of Formula (I) which are the object of the present invention are prepared by means of the condensation of 7-t-butoxyiminomethylcamptothecin (indicated as "7-t-but-CP"), possibly functionalised via a suitable bridge (indicated as "$U_1$-$X_1$"), with a cyclopeptide derivative (indicated as "$Y_1$").

The condensation reactions can be carried out according to one of the following reaction schemes:

7-t-but-CP+$U_1$-$X_1$-$Y_1$ or 7-t-but-CP-$U_1$+$X_1$-$Y_1$ or 7-t-but-CP-$U_1$-$X_1$+$Y_1$ or 7-t-but-CP+$U_1$+$X_1$+$Y_1$ or 7-t-but-CP-$U_1$+$X_1$+$Y_1$;

where 7-t-but-CP represents 7-t-butoxyiminomethylcamptothecin, $U_1$, $X_1$ and $Y_1$ represent respectively the groups U, X and Y as defined in Formula I, eventually appropriately functionalised and/or protected so that the conjugated compounds of Formula I are obtained.

These reactions are conducted using conventional methods, such as, for instance, those described *Journal of Controlled Release* 2003, 91, 61-73; S. S. Dharap et al.; *Journal of Medicinal Chem.* 2003, 46, 190-3, R. Bhatt;

The cyclopeptides $Y_1$ can be prepared according to conventional peptide synthesis techniques, as described in examples 1 to 6. The peptide synthesis can be accomplished either in the solid phase or in solution.

Once the desired cyclopeptide has been obtained, it will be used in the condensation reaction in its protected form, and the protector groups will be removed only after obtaining the final compound. The deprotection is done using known methods, e.g. acid conditions by means of the use of pure trifluoroacetic acid or in the presence of chlorinated organic solvents.

The compounds described in the present invention are topoisomerase I inhibitors and are therefore useful as medicaments, particularly for the treatment of diseases that benefit from the inhibition of said topoisomerase. In particular, the compounds according to the present invention exhibit antiproliferative activity, and therefore are used for their therapeutic properties, and possess physicochemical properties which make them suitable for formulation in pharmaceutical compositions.

The pharmaceutical compositions contain at least one formula (I) compound as an active ingredient, in an amount such as to produce a significant therapeutic effect. The compositions covered by the present invention are entirely conventional and are obtained using methods that are common practice in the pharmaceutical industry. According to the administration route opted for, the compositions will be in solid or liquid form and suitable for oral, parenteral or intravenous administration. The compositions according to the present invention contain, along with the active ingredient, at least one pharmaceutically acceptable vehicle or excipient. Formulation adjuvants, such as, for example, solubilising agents, dispersing agents, suspension agents or emulsifying agents may be particularly useful.

The compounds of Formula (I) can also be used in combination with other active ingredients, such as, for example, anticancer agents or other drugs with antiparasitic or antiviral activity, both in separate forms and in a single dosage form.

The compounds according to the present invention are useful as medicaments with anticancer activity, e.g. in non-microcytoma and small-cell lung cancer, or in colorectal or prostate cancer, glioblastoma and neuroblastoma, cervical cancer, ovarian cancer, gastrointestinal carcinoma, carcinoma of the liver, Kaposi's sarcoma, renal carcinoma, sarcoma and osteosarcoma, testicular carcinoma, carcinoma of the breast, carcinoma of the pancreas, melanoma, carcinoma of the urinary bladder and of the head and neck. One of the advantages afforded by the compounds according to the present invention is the combination of antitopoisomerase activity, proper to the camptothecin portion of the molecule, and the integrin inhibiting activity, provided by the cyclopeptide portion of the molecule. The result is the possible combined action of the compounds according to the present invention which will be favourably received in the oncological sector by the experts operating in that sector. In fact, the cyclopeptide portion, containing the Arg-Gly-Asp sequence, not only directs the molecule against tumours expressing integrins, but, once the target has been reached, is capable of exerting multiple functions, ranging from the internalisation of the cytotoxic portion of the molecule to integrin inhibiting activity, with the resulting advantages, particularly in terms of the inhibition of tumour angiogenesis. The cyclopeptide portion, once separated from the camptothecin portion, is also capable of exerting its action at a distance from the site of the tumour, and therefore the compounds according to the present invention also prove useful in the prevention or treatment of metastatic forms.

The medicaments which are the object of the present invention can also be used in the treatment of parasite diseases.

The following examples further illustrate the invention.

The abbreviations used are the following:
Aad (aminoadipic acid);
Amb (aminomethylbenzyl);
Amp (aminomethylphenylalanine);
Boc (tert-butoxycarbonyl);
CSA (camphosulfonic acid);
CTH (catalytic transfer hydrogenation);
DCC (dicyclohexylcarbodiimide);
DCM (dichloromethane);
DIEA (diisopropylethylamine);
DMF (dimethylformamide);
Dy(OTf)$_3$ dysprosium triflate;
Fmoc (9-fluorenylmethyloxycarbonyl);
HOBT (hydroxybenzotriazole);
NMP (N-methyl-pyrrolidone);
Pht (phthaloyl);
Pmc (pentamethylchroman-6-sulphonyl);
ST1481 (7-t-butoxyiminomethylcamptothecin, also named gimatecan)
TBTU (tetrafluoroborate-O-benzotriazol-1-yl-tetramethyluronium);
TFA (trifluoroacetic acid).

EXAMPLES

Example 1

Synthesis of c(Arg(Pmc)-Gly-Asp(OtBu)-D-Phe-Amp) (Protected ST2581)

1.587 mmol of Fmoc-Gly-Res (Res=Sasrin Resin@, Bachem) were suspended under stirring in 75 ml of DMF for 30 minutes, after which 18 ml of piperidine were added, continuing the stirring for a further 30 minutes. The resin, filtered and washed with DMF, was suspended in 50 ml of NMP (N-methyl-pyrrolidone) for 15 minutes, after which Fmoc-Arg(Pmc)-OH, HOBT, TBTU and DIEA were added (3.174 mmol of each); after 2 hours of stirring, the suspension was filtered and washed with DMF. After deprotection with piperidine, the coupling was repeated with the other amino acids in succession, operating each time as described above, namely: Fmoc-Amp(Cbz)-OH, Fmoc-D-Phe-OH, and Fmoc-Asp(OtBu)-OH. After the last deprotection of the Fmoc-N-terminal, the linear pentapeptide was released from the resin with 45 ml of 1% TFA in DCM. This was dissolved in approximately 1 l of $CH_3CN$, and 4.761 mmol of HOBT and TBTU and 10 ml of DIEA were added; the solution was kept under stirring for 30 minutes, the solvent was evaporated to a small volume and the precipitation of the product was completed with water. The filtered crude product was dissolved in 27 ml of a mixture of MeOH and DMF 1:1; 5 mmol of ammonium formiate and 0.55 g of 10% Pd/C were added and left under stirring at room temperature for 30 minutes. The suspension was filtered on celite and brought to dryness. The residue was purified by preparatory RP-HPLC (column: Alltima®C-18, Alltech; mobile phase 50% $CH_3CN$ in water +0.1% TFA; retention time (Rt)=9.13 minutes). 483 mg of a white powder were obtained.

$^1$H-NMR (DMSO-d$_6$)δ8.3, 8.07, 8.04, 7.90, 7.80, 7.33, 7.15, 7.07, 4.62, 4.50, 4.35, 4.12, 4.01, 3.15, 3.03, 2.96-2.65, 2.58, 2.48, 2.32, 2.02, 1.75, 1.50, 1.35, 1.23. Molecular mass (Maldi-Tof): 973

Example 2

Synthesis of c(Arg(Pmc)-Gly-Asp(OtBu)-D-Phe-Aad) (protected ST2650)

0.69 mmol of Fmoc-Gly-Res were treated exactly as described in example 1, with the difference that in this case the third and fourth amino acids were added in the form of dipeptide Fmoc-D-Phe-Aad(OBzl)-OH. After deprotection by means of CTH, and purification of the crude product with preparatory RP-HPLC (mobile phase: 66% $CH_3CN$ in water+ 0.1% TFA; Rt=17.29 minutes), 187 mg of pure peptide were obtained.

$^1$H-NMR (DMSO-$d_6$)δ 7.23, 4.58, 4.20-3.90, 3.28, 3.05, 2.99, 2.85, 2.74-2.35, 2.15, 2.05, 1.85-1.25. Molecular mass (Maldi-Tof): 940

Example 3

Synthesis of c(Arg(Pmc)-Gly-Asp (OtBu)-D-Phe-N-Me-Amp) (Protected ST2700)

To a suspension of Fmoc-Phe(4-Pht-N-$CH_2$)—COOH in anhydrous toluene brought to reflux 2 eq of CSA and 20 eq of paraformaldehyde were added, divided into 4 portions at intervals of 15 minutes. The mixture was left to cool, diluted with 120 ml of toluene and washed with 5% $NaHCO_3$ and water. After evaporation of the solvent, the residue was dissolved in 15 ml of $CHCL_3$+15 ml of TFA+700 μl of $Et_3SiH$; the mixture was left in the dark to stir for 42 hours. After evaporation of the solvent, the residue was purified by filtration on silica gel. Overall yield: 90%.

The linear peptide was synthesized in solid phase as described in example 1, inserting Fmoc-N-Me-Phe-(4-Pht-N-$CH_2$)—COOH as the third amino acid, prepared as described above. In this case the deprotections of N-Fmoc-terminal on resin were carried out with 30% diisopropylamine (300 eq) in solution in DMF (owing to the presence of phthalimide). After cyclisation, 500 mg of the peptide were dissolved hot in 10 ml of absolute EtOH, to which 0.9 ml of a solution of $NH_2$-$NH_2$.$H_2O$ 1 M in ethanol was added. After heating at reflux for 2 hours, the solvent was evaporated and the residue taken up with 10 ml of DCM+10 ml of $Na_2CO_3$ solution under vigorous shaking. The crude final product was recovered from the organic phase after evaporation and purified by preparatory RP-HPLC (mobile phase: 52% $CH_3CN$ in water+0.1% TFA; Rt=10 minutes).

$^1$H-NMR ($CDCl_3$)δ 8.29-7.66, 7.38-7.07, 4.95-4.77, 4.09, 3.41, 3.05-2.81, 2.51, 2.05, 1.74, 1.40, 1.26. Molecular mass (Maldi-Tof): 987

Example 4

Synthesis of c[Arg(Pmc)-Gly-Asp-(OtBu)-D-Phe-Amp(CO—($CH_2$)$_2$—COOH)](Protected ST2649)

120 mg of cyclopeptide c[Arg(Pmc)-Gly-Asp(OtBu)-D-Phe-Amp]·TFA (prepared as described in example 1) were dissolved in 3.6 ml of a mixture of DCM-DMF 2:1, together with a stoichiometric amount of TEA and succinic anhydride. After 1 hour the reaction mixture was diluted with 30 ml of DCM and washed with water. The organic phase, dried and concentrated, yielded a residue of 100 mg of pure product.

Analytical RP-HPLC: column: Purosphere STAR®, Merck; mobile phase: 45% $CH_3CN$ in water+0.1% TFA; Rt=13.17 minutes.

$^1$H-NMR(DMSO-$d_6$)δ8.20-7.75, 7.19-7.02, 4.58, 4.45, 4.36, 4.30, 4.20, 4.05, 3.00, 2.97-2.57, 1.83, 1.62, 1.32. Molecular mass (Maldi-Tof): 1073

Example 5

Synthesis of c(Arg(Pmc)-Gly-Asp(OtBu)-D-Phe-N-Amb-Gly) (Protected ST2701)

To a solution of 1-22 mmol of Boc-monoprotected p-xylylenediamine in 6 ml of THF were added 1.83 mmol of TEA and, dropwise, a solution of 1.22 mmol of benzyl bromoacetate in 2 ml of THF. The mixture was left under stirring overnight, after which the solvent was evaporated and the residue purified on a flash column ($CHCl_3$-EtOAc, 9:1). 0.69 mmol of N-(4-Boc-NH-$CH_2$-benzyl)-glycine benzylester were obtained.

250 mg of Fmoc-D-Phe-OH were dissolved in 27 ml of DCM and 40 μl of diphosgene and 230 μl of sym-collidine were added; after 15 minutes 190 mg of the previously prepared ester were added, dissolved in 3 ml of DCM. After 3 hours, 80 μl of N-Me-piperazine were added to the reaction mixture and stirred for 10 minutes, after which the mixture was diluted with 10 ml of DCM and extraction was done with water, HCl 0.5N, water, 5% $NaHCO_3$ and water. After evaporation of the solvent, the residue was purified by flash chromatography on silica gel (DCM-EtOAc, 9:1). Yield: 80%.

To 100 mg of the product thus obtained, dissolved in 6 ml of MeOH, were added 76 μl of AcOH and 42 mg of $HCOONH_4$, and the mixture cooled to 0° C., and 50 mg of 10% Pd/C were added. After 30 minutes, the reaction mixture was filtered on celite. The filtrate was brought to dryness and purified on a flash column ($CHCl_3$-MeOH 9:1). Yield: 90%.

190 mg of the product thus obtained were dissolved in 1.2 ml of TFA and brought to dryness (deprotection of Boc); the residue was redissolved in 9 ml of 10% $Na_2CO_3$+6 ml of dioxane, cooled to 0° C. and a solution of 120 μl of benzyloxycarbonyl chloride diluted with 3 ml of dioxane was added dropwise. After 1 hour stirring at room temperature, evaporation was carried out under vacuum to a small volume, after which the mixture was diluted with water, the pH was reduced to 1 with HCl and extraction was done with EtOAc. After evaporation of the solvent, the residue was purified by filtration on silica gel, washing with $CHCl_3$-MeOH (8:2). Pure dipeptide yield: 82%.

0.69 mmol of Fmoc-Gly-Res were treated as described in example 1. After Arg, the previously prepared dipeptide Fmoc-D-Phe-N(4-Cbz-NH—$CH_2$-benzyl)-Gl was added in sequence. After deprotection of Cbz by means of CTH, the crude product c(Arg(Pmc)-Gly-Asp(OtBu)-D-Phe-N-Amp-Gly) was purified by preparatory RP-HPLC (mobile phase: 50% $CH_3CN$ in water+0.1% TFA; Rt=10.5 minutes).

$^1$H-NMR (DMSO-$d_6$)δ8.29-7.66, 7.44-6.90, 5.15, 4.72-4.18, 4.20, 4.05-3.32, 3.15, 3.06, 2.70, 2.51, 2.49, 2.01, 1.80-1.35, 1.49, 1.35, 1.23. Molecular mass (Maldi-Tof): 973

Example 6

Synthesis of c(Arg(Pmc)-Gly-Asp(OtBu)-D-Phe-Amp(CO—$CH_2$—(O$CH_2CH_2$)$_n$—O—$CH_2$—COOH))

To a solution of 200 mg of c(Arg(Pmc)-Gly-Asp(OtBu)-D-Phe-Amp)·TFA (obtained as described in example 1) in 4 ml of a 3:1 DCM-DMF mixture was added a substantial excess of glycol diacid. DIEA (3 eq) and DCC (2 eq) were added to the same solution. The mixture was left under stirring overnight, after which it was diluted with DCM and washed with water.

The crude product was recovered by evaporating the organic phase and purified by flash chromatography (mobile phase: $CHCl_3$-MeOH 7:3+1% AcOH); the fractions containing the product were pooled, washed with water, dehydrated and brought to dryness, and yielded a residue of 157 mg of pure product.

Analytical RP-HPLC: (column: Purosphere STAR®, Merck; mobile phase: 50% CH$_3$CN 50% in water+0.1% TFA; R$_t$=10.96)

$^1$H-NMR (DMSO-d$_6$)δ8.35-7.92, 7.20-7.00, 4.65, 4.50, 3.94, 3.60-3.45, 3.00-2.60, 2.55, 2.45, 2.30, 2.00, 1.70, 1.50, 1.30, 1.20. Molecular mass (Maldi-Tof): corresponding to the different glycols used of various molecular weights.

Synthesis of Gimatecan Derivatives

Example 7

Synthesis of 20-O-Val-gimatecan-ST2678

One mmol of ST1481 prepared as described in Example 2 of patent EP 1 044 977, 0.6 mmol of Dy(OTf)$_3$, 3 mmol of dimethylaminopyridine and 3 mmol of Boc-Val-OH were suspended in 15 ml of anhydrous CH$_2$Cl$_2$ and brought to −10° C.; after 30 minutes 3.1 mmol of DCC were added and after another 30 minutes at −10° C. the reaction mixture was heated to room temperature. After 2 hours the reaction was diluted with another 20 ml of CH$_2$Cl$_2$, washed with 1N HCl, with NaHCO$_3$ and dried on Na$_2$SO$_4$. The crude product was purified by chromatography on SiO$_2$ with CH$_2$Cl$_2$/MeOH 97:3 to give the product as a yellow solid with a yield of 92%. Rf=0.72 in CH$_2$Cl$_2$/MeOH 96:4.

Analytical RP-HPLC: (column: Luna C18, Phenomenex®; mobile phase: 45% CH$_3$CN in water; Rt=23.0)

$^1$H-NMR (CDCl$_3$)δ9.05, 8.3-8.2, 7.9-7.7, 7.3, 5.8-5.7, 5.5-5.4, 5.05-4.95, 4.4-4.3, 2.4-2.2, 1.6-1.4, 1.1-0.9. Molecular mass (ESI): 646

The intermediate product ST2678 [N-Boc] is deprotected in DCM/TFA (75/25) at 0° C., with a quantitative yield. The ST 2678 thus obtained can be used to bind RGD derivatives directly or as a further intermediate, which can be used to bind a second residue (see examples 8-9).

Example 8

Synthesis of 20-O-Val-Asp-gimatecan-ST2676 [N-Boc]

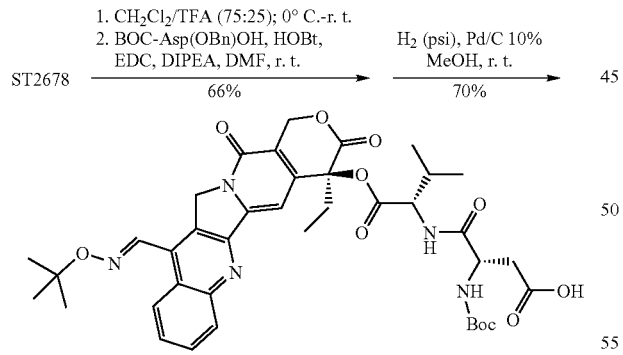

One mmol of ST2678 and 3.7 mmol of DIPEA were added in that order to a solution of 1.2 mmol of suitably protected aspartic acid, 1.8 mmol of HOBt and 1.4 mmol of EDC in DMF at 0° C. The reaction mixture was left overnight at room temperature before being partitioned between water and dichloromethane, and the crude product thus obtained was purified by chromatography on SiO$_2$ with CH$_2$Cl$_2$/MeOH 96:4 to give the product as a yellow solid with a yield of 66%. Rf=0.5 in CH$_2$Cl$_2$/MeOH 96:4

Analytical RP-HPLC: (column: Luna C18, Phenomenex®; mobile phase: 45% CH$_3$CN in water; Rt=23.3).

$^1$H-NMR (CDCL$_3$)δ9.05, 8.3-8.2, 7.9-7.7., 7.4-7.2, 6.0-5.9, 5.7-5.6, 5.5-5.4, 5.1, 4.8-4.7, 4.6-4.5, 3.3-3.1, 3.0-2.8, 2.4-2.2, 1.6-1.4, 1.-0.9. Molecular mass: (ESI): 851

Deprotection of the Carboxyl Group

The benzylester was hydrogenolysed with H$_2$/10%Pd-C at 20 psi with a yield of 70% after purification with CH$_2$Cl$_2$/MeOH 94:6. Rf=0.52 in CH$_2$Cl$_2$/MeOH 92:8.

Analytical RP-HPLC: (column: Luna C18, Phenomenex®; mobile phase: 45% CH$_3$CN in water; Rt=22.9)

$^1$H-NMR (CDCl$_3$)δ9.05, 8.3-8.2, 7.9-7.7, 7.5, 6.0-5.9, 5.7-5.6, 5.5-5.4, 4.8-4.7, 4.5-4.4, 3.3-3.1, 2.9-2.8, 2.4-2.2, 1.6-1.4, 1.1-0.9. Molecular mass (ESI): 761

Example 9

Synthesis of Compound [ST2677]

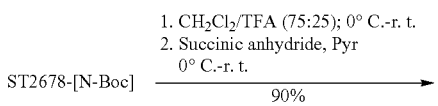

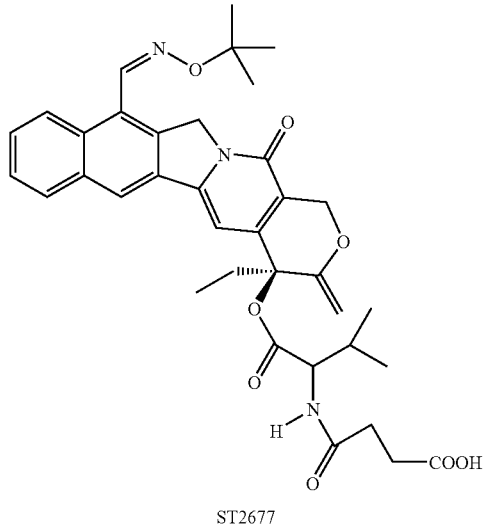

One mmol of deprotected ST2678-[N-Boc] was dissolved in 10 ml of anhydrous pyridine and after bringing the solution to 0° C., 2.5 mmol of succinic anhydride were added: the mixture was restored to room temperature for 1 hour. The solvent was removed, the residue was taken up with CH$_2$Cl$_2$ and the organic phase was washed with 0.5N HCl. The crude product was purified by chromatography on SiO$_2$ with CH$_2$Cl$_2$/MeOH 95:5 to give the expected product as a yellow solid with a yield of 90%. Rf=0.41 in CH$_2$Cl$_2$/MeOH 92:8.

Analytical RP-HPLC: (column; Luna C18, Phenomenex®; mobile phase: 45% CH$_3$CN in water; Rt=17.0)

$^1$H-NMR (CDCl$_3$)δ9.05, 8.4-8.2, 7.9-7.7, 7.5, 6.4-6.3, 5.7-5.6, 5.5-5.4, 4.6-4.5, 3.7, 3.0-2.1, 1.5, 1.1-0.9. Molecular mass (ESI): 646

Synthesis of Conjugated Derivatives

Example 10

Synthesis of Compounds ST2670 (or ST2671)

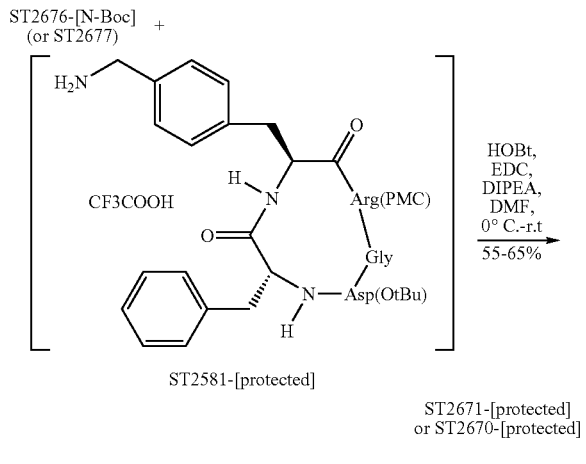

The same synthesis process was used for both.

To a solution of 1.2 mmol of ST2676 [N-Boc] (or ST 2677) in anhydrous DMF cooled to 0° C. were added 2.1 mmol of HOBt and 1.4 mmol of EDC and the resulting mixture was stirred for 30 minutes before adding 1 mmol of ST2581 and DIPEA in sequence. After being left overnight the mixture was partitioned between water and dichloromethane and the organic phase was then dried on $Na_2SO_4$ and the crude product purified by chromatography on $SiO_2$ with $CH_2Cl_2$/MeOH 92:8 to give the expected product, protected ST2670 (or protected ST2671), with a yield ranging from 55% to 65%.

Analytical RP-HPLC: (column: Luna C18, Phenomenex®; mobile phase: 45% $CH_3CN$ in water; Rt=20.1 for protected ST2670 and Rt=23.2 for protected ST2671) Molecular mass (ESI): 1718 for protected ST2671Molecular mass (ESI): 1601 for protected ST2670

Deprotection of Conjugated Products

The final deprotection to obtain the two compounds ST2670 and ST2671 was done for both compounds with $CH_2Cl_2$/TFA 1:1 for 2 hours bringing the mixture from 0° C. to room temperature; this operation was followed by a step on ion-exchange resin which gave the products as hydrochlorides.

Analytical RP-HPLC: (column: Luna C18, Phenomenex®; mobile phase: 35% $CH_3CN$ in water; Rt=14.5 for ST2670 and Rt=14.3 for ST2671) Molecular mass (ESI): 1294 for ST2671

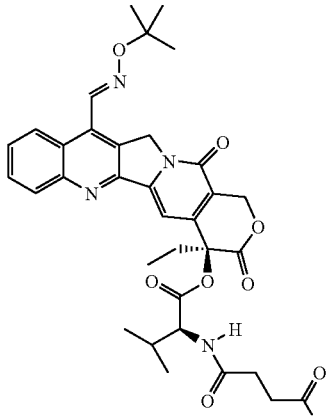

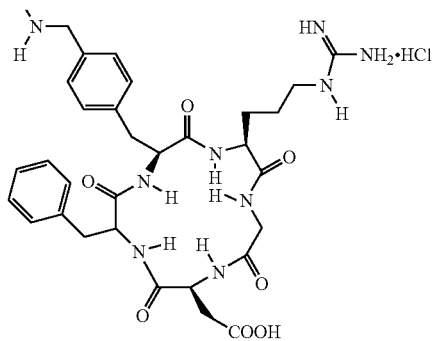

ST2670

-continued

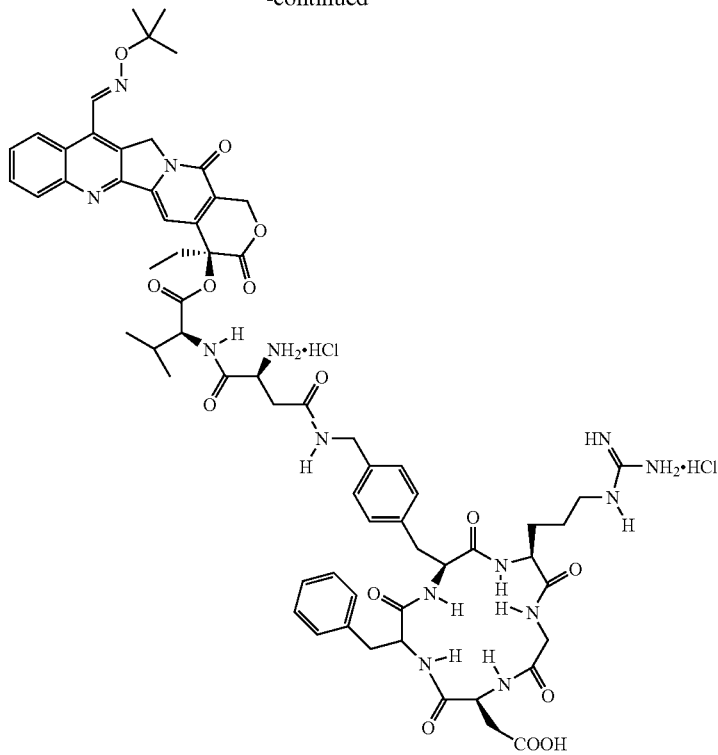

ST2671

Molecular mass (ESI): 1279 for ST2670

Biological Results

Binding to Integrin $\alpha_v\beta_3$ Receptors

The purified $\alpha_v\beta_3$ receptor (Chemicon, cat. CC1020) was diluted in buffer (20 mM Tris, pH 7.4, 150 mM NaCl, 2 mM $CaCl_2$, 1 mM $MgCl_2$, 1 mM $MnCl_2$) at a concentration of 0.5 μg/ml. An aliquot of 100 μl was added to 96-well plates and incubated overnight at +4° C. Plates were washed once with buffer (50 mM Tris, pH 7,4, 100 mM NaCl, 2 mM $CaCl_2$, 1 mM $MgCl_2$, 1 mM $MnCl_2$, 1% bovine serum albumin) and then incubated for another 2 hours at room temperature. Plates were washed twice with the same buffer and incubated for 3 hours at room temperature with the radioactive ligand [$^{125}$I]echistatin (Amersham Pharmacia Biotech) 0.05 nM in the presence of competition ligands. At the end of incubation, the wells were washed and the radioactivity determined using a gamma counter (Packard). Non-specific binding of the ligand was determined in the presence of excess cold echistatin (1 μM).

Binding to Integrin $\alpha_v\beta_5$ Receptors

The purified $\alpha_v\beta_5$ receptor (Chemicon, cat. CC1020) was diluted in buffer (20 mM Tris, pH 7.4, 150 mM NaCl, 2 mM $CaCl_2$, 1 mM $MgCl_2$, 1 mM $MnCl_2$) at a concentration of 1 μg/ml. An aliquot of 100 μl was added to 96-well plates and incubated overnight at +4° C. Plates were washed once with buffer (50 mM Tris, pH 7.4, 100 mM NaCl, 2 mM $CaCl_2$, 1 mM $MgCl_2$, 1 mM $MnCl_2$, 1% bovine serum albumin) and then incubated for another 2 hours at room temperature. Plates were washed twice with the same buffer and incubated for 3 hours at room temperature with the radioactive ligand [$^{125}$I]echistatin (Amersham Pharmacia Biotech) 0.15 nM in the presence of competition ligands. At the end of incubation, the wells were washed and the radioactivity determined using a gamma counter (Packard). Non-specific ligand binding was determined in the presence of excess cold echistatin (1 μM).

Evaluation of $IC_{50}$ Parameters

The affinity of the products for vitronectin receptors was expressed as $IC_{50}$ value±SD, i.e. as the concentration capable of inhibiting 50% of the specific radioligand-receptor binding. The $IC_{50}$ parameter was elaborated using "ALLFIT" software.

Results

The following tables give the results of the affinity of camptothecin-RGD conjugates and RGD peptides for vitronectin $\alpha_v\beta_3$ and $\alpha_v\beta_5$ receptors. The conjugates showed a potent affinity on both integrin receptors comparable to that observed with RGD peptides.

TABLE 1

Affinity of camptothecin-RGD conjugates for vitronectin $\alpha_v\beta_3$ and $\alpha_v\beta_5$ receptors

| Compound | $\alpha_v\beta_3$ | $\alpha_v\beta_5$ |
| --- | --- | --- |
| | $IC_{50}$ ± DS (nM) | |
| ST2670 | 47.7 ± 0.9 | 74 ± 0.8 |
| ST2671 | 22.8 ± 1.2 | 54.2 ± 0.5 |

TABLE 2

Affinity of RGD peptides for vitronectin $\alpha_v\beta_3$ and $\alpha_v\beta_5$ receptors

| Compound | $\alpha_v\beta_3$ | $\alpha_v\beta_5$ |
|---|---|---|
| | $IC_{50}$ ± SD (nM) | |
| ST2581 | 1.7 ± 0.1 | 3.4 ± 0.1 |
| ST2650 | 28.6 ± 0.7 | 0.17 ± 0.01 |
| ST2700 | 7.2 ± 0.07 | 0.9 ± 0.005 |
| ST2649 | 37.6 ± 0.9 | 5.1 ± 0.07 |
| ST2701 | 36.7 ± 0.7 | 2.9 ± 0.1 |

Cytotoxicity of the Conjugates on Different Tumor Cell Lines

To evaluate the effect of the compound on survival cells, the sulphorodamine B test was used. To test the effects of the compounds on cell growth, PC3 human prostate carcinoma, A498 human renal carcinoma, A2780 human ovarian carcinoma cells and NCI-H460 non-small cell lung carcinoma were used. A2780, NCI-H460 and PC3 tumor cells were grown RPMI 1640 containing 10% fetal bovine serum (GIBCO), whereas A498 tumor cells were grown in EMEM containing 10% fetal bovine serum (GIBCO).

Tumor cells were seeded in 96-well tissue culture plates (Corning) at approximately 10% confluence and were allowed to attach and recover for at least 24 h. Varying concentrations of the drugs were then added to each well to calculate their IC50 value (the concentration which inhibits the 50% of cell survival). The plates were incubated for 72 h at 37° C. or 2 h followed by 72 h of recovery. At the end of the treatment, the plates were washed by removal of the surnatant and addition of PBS 3 times. 200 μl PBS and 50 μl of cold 80% TCA were added. The plates were incubated on ice for at least 1 h. TCA was removed, the plates were washed 3 times for immersion in distilled-water and dried on paper and at 40° C. for 5 min.

Then 200 μl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min.

Then 200 μl Tris 10 mM were added, the plates were kept under stirring for 20 min. The survival cell was determined as optical density by a Multiskan spectrofluorimeter at 540 nm. The amount of cells killed was calculated as the percentage decrease in sulphorodamine B binding compared with control cultures.

The $IC_{50}$ values were calculated with the "ALLFIT" program.

The conjugate ST2670 showed the most potent cytotoxic activity on A2780 ovarian tumor cells with an IC50 value of 0.4 μM. Moreover, the conjugate ST2670 showed a comparable cytotoxicity to that observed with ST2677 (free camptothecin) on tumor cells (Table 3). The conjugate ST2671 also revealed a potent cytotoxicity on PC3 tumor cells comparable to that found with the free camptothecin ST2676.

TABLE 3

Cytotoxicity of the conjugates ST2670 and ST2671 and of the free camptothecins (ST2676 and ST2677) on PC3, A498 and A2780 tumor cells (72 h of treatment)

| Compound | PC3 | A498 | A2780 |
|---|---|---|---|
| | IC50 ± SD, μM | | |
| ST2670 | 9.6 ± 0.6 | 1.6 ± 0.3 | 0.4 ± 0.05 |
| ST2671 | 0.35 ± 0.08 | n.d. | n.d. |

TABLE 3-continued

Cytotoxicity of the conjugates ST2670 and ST2671 and of the free camptothecins (ST2676 and ST2677) on PC3, A498 and A2780 tumor cells (72 h of treatment)

| Compound | PC3 | A498 | A2780 |
|---|---|---|---|
| | IC50 ± SD, μM | | |
| ST2676 | 0.038 ± 0.004 | 0.047 ± 0.005 | <0.00097 |
| ST2677 | 5.42 ± 0.55 | 1.37 ± 0.3 | 0.079 ± 0.003 | n.d. = not determined.

TABLE 4

Cytotoxicity of the free camptothecins 20-O derivatives (ST2676, ST2677, ST2678) on H460 non-small cell lung carcinoma cells (2 h of treatment)

| Compound | NCI-H460 $IC_{50}$ ± SD, μM |
|---|---|
| ST2676 | 0.17 ± 0.02 |
| ST2677 | >1 |
| ST2678 | 0.025 ± 0.002 |

The invention claimed is:

1. Compounds of Formula (I)

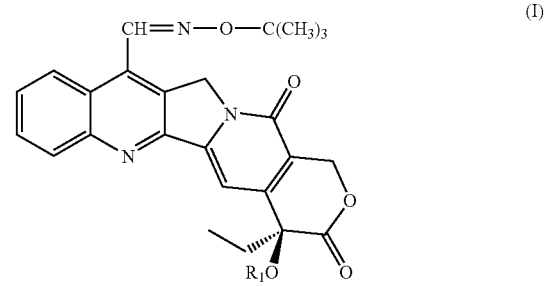

(I)

where:
R$_1$ is the U-X—Y group, in which:
U is one of the following groups —COCHR$_{10}$NH— or CON[(CH$_2$)$_{n2}$NHR$_7$]—CH$_2$—, where R$_{10}$ is H or is selected from the group consisting of: linear or branched C$_1$-C$_4$ alkyl, optionally substituted with C$_6$-C$_{14}$ aryl or an amino-alkyl C$_1$-C$_4$; R$_7$ is H or linear or branched C$_1$-C$_4$ alkyl; n$_2$ is an integer number from 2 to 6;
X is H or is a group selected among the following: —COCHR$_3$NH—, —COCHR$_6$(CH$_2$)$_{n3}$R$_4$—, —R$_4$—CH$_2$(OCH$_2$CH$_2$)$_{n4}$OCH$_2$R$_4$—, —R$_4$(Q)R$_4$—, —R$_5$[Arg-NH(CH$_2$)$_{n5}$CO]$_{n6}$R$_5$—, —R$_5$—[N-guanidinopropyl-Gly]$_{n6}$R$_5$—, in which n$_3$ is an integer number from 0 to 5, n$_4$ is an integer number from 0 to 50, n$_5$ is an integer number from 2 to 6, n$_6$ is an integer number from 2 to 7;
R$_3$ is H or linear or branched C$_1$-C$_4$ alkyl, optionally substituted with —COOH, —CONH$_2$, —NH$_2$ or —OH;
R$_4$ is selected from the group consisting of: —NH—, —CO—, —CONH—, —NHCO—;

$R_5$ is either absent or is the group —$R_4(Q)R_4$—;

$R_6$ is H or $NH_2$;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is absent or H or is the following group c(Arg-Gly-Asp-$AA_1$-$AA_2$), in which:

c means cyclic;

$AA_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-$CF_3$-Phe, (D)-4-acetylamine-Phe;

$AA_2$ is selected from the group consisting of: NW—CH[$(CH_2)_{n7}$—CO]—CO, NW—CH[$(CH_2)_{n7}$—NH]—CO, NW—[4—$(CH_2)_{n7}$—CO]-Phe, NW—[4—$(CH_2)_{n7}$—NH]-Phe, [NW]-Gly, NW-Val, in which W is selected from H, linear or branched $C_1$-$C_6$ alkyl, —$(CH_2)_{n7}$—COOH where $n_7$ is an integer number from 0 to 5, 4-carboxybenzyl, 4-aminomethylbenzyl; the $N_1$-oxides, racemic mixtures, their single enantiomers, their single diastereoisomers, the forms E and Z, mixtures thereof, and their pharmaceutically acceptable salts.

2. A compound according to claim 1, having the following formula:

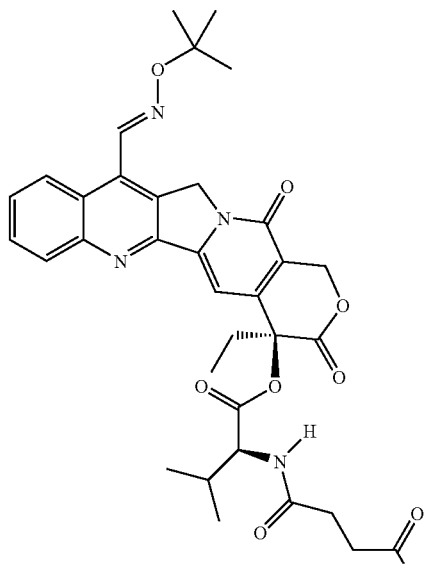

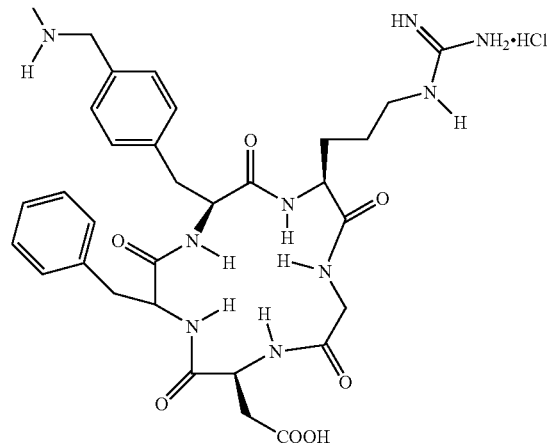

ST2670 the $N_1$-oxides, racemic mixtures, their single enantiomers, their single diastereoisomers, the forms E and Z, mixtures thereof, and its pharmaceutically acceptable salts.

3. A compound according to claim 1, having the following formula:

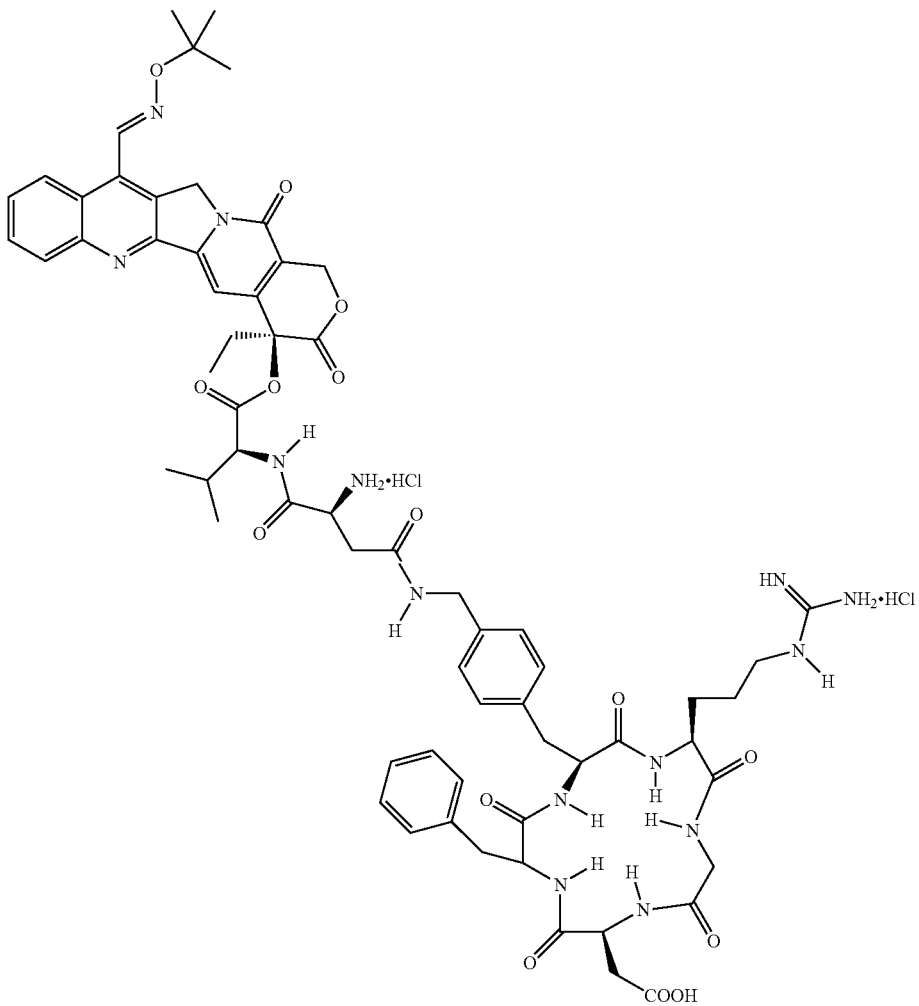

ST2671 the $N_1$-oxides, racemic mixtures, their single enantiomers, their single diastereoisomers, the forms E and Z, mixtures thereof, its pharmaceutically acceptable salts.

4. A pharmaceutical composition containing at least one compound according to claim 1 as the active ingredient in a mixture with at least one pharmaceutically acceptable excipient and/or vehicle.

5. A method of treating non-small cell lung cancer, prostate cancer, ovarian carcinoma, or renal carcinoma, comprising administering to a subject an effective amount of a compound of claim 1.

6. Process for the preparation of compounds of Formula I

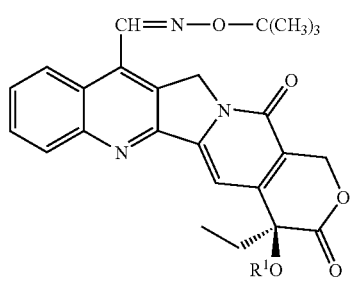

Formula I where:
  $R_1$ is the U—X—Y group, in which:
  U is one of the following groups —COCHR$_{10}$NH— or CON[(CH$_2$)$_{n2}$NHR$_7$]—CH$_2$—, where $R_{10}$ is H or is selected from the group consisting of: linear or branched $C_1$-$C_4$ alkyl, optionally substituted with $C_6$-$C_{14}$ aryl or an amino-alkyl $C_1$-$C_4$; $R_7$ is H or linear or branched $C_1$-$C_4$ alkyl; $n_2$ is an integer number from 2 to 6;
  X is H or is a group selected among the following: —COCHR$_3$NH—, —COCHR$_6$(CH$_2$)$_{n3}$R$_4$—, —R$_4$—CH$_2$(OCH$_2$CH$_2$)$_{n4}$OCH$_2$R$_4$—, —R$_4$(Q)R$_4$—, —R$_5$[Arg -NH(CH$_2$)$_{n5}$CO]$_{n6}$R$_5$—, —R$_5$-[N-guanidinopropyl-Gly]$_{n6}$R$_5$—, in which $n_3$ is an integer number from 0 to 5, $n_4$ is an integer number from 0 to 50, $n_5$ is an integer number from 2 to 6, $n_6$ is an integer number from 2 to 7;
  $R_3$ is H or linear or branched $C_1$-$C_4$ alkyl, optionally substituted with —COOH, —CONH$_2$, —NH$_2$ or —OH;
  $R_4$ is selected from the group consisting of: —NH—, —CO—, —CONH—, —NHCO—;
  $R_5$ is either absent or is the group —R$_4$(Q)R$_4$—;
  $R_6$ is H or NH$_2$;
  Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is absent or H or is the following group c(Arg-Gly-Asp-$AA_1$-$AA_2$), in which:

c means cyclic;

$AA_1$ is selected from the group consisting of: (D)-Phe, (D)-Trp, (D)-Tyr, (D)-2- naphthylAla, (D)-4-terbutyl-Phe, (D)-4,4'-biphenyl-Ala, (D)-4-$CF_3$-Phe, (D)-4-acetylamine-Phe;

$AA_2$ is selected from the group consisting of: NW—CH[($CH_2$)$_{n7}$—CO]CO, NW—CH[($CH_2$)$_{n7}$—NH]—CO, NW—[4—($CH_2$)$_{n7}$—CO]-Phe, NW—[4—($CH_2$)$_{n7}$—NH]-Phe, [NW]-Gly, NW-Val, in which W is selected from H, linear or branched $C_1$-$C_6$ alkyl, —($CH_2$)$_{n7}$—COOH where $n_7$ is an integer number from 0 to 5, 4-carboxybenzyl, 4-aminomethylbenzyl;

the $N_1$-oxides, racemic mixtures, its single enantiomers, its single diastereoisomers, the forms E and Z, mixtures thereof, and its pharmaceutically acceptable salts;

carried out according to the following reaction scheme:

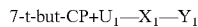

7-t-but-CP+$U_1$—$X_1$—$Y_1$ where 7-t-but-CP represents 7-t-butoxyiminomethylcamptothecin, $U_1$, $X_1$ and $Y_1$ represent respectively the groups U, X and Y as defined above.

7. Process for the preparation of compounds of Formula I

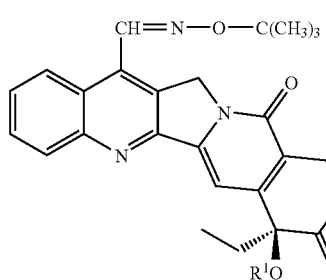

Formula I where:

$R_1$ is the U-X-Y group, in which:

U is one of the following groups —COCHR$_{10}$NH— or CON[($CH_2$)$_{n2}$NHR$_7$]—CH$_2$—, where $R_{10}$ is H or is selected from the group consisting of: linear or branched $C_1$-$C_4$ alkyl, optionally substituted with $C_6$-$C_{14}$ aryl or an amino-alkyl $C_1$-$C_4$; $R_7$ is H or linear or branched $C_1$-$C_4$ alkyl; $n_2$ is an integer number from 2 to 6;

X is H or is a group selected among the following: —COCHR$_3$NH—, —COCHR$_6$($CH_2$)$_{n3}$R$_4$—, —R$_4$—CH$_2$(OCH$_2$CH$_2$)$_{n4}$OCH$_2$R$_4$—, —R$_4$(Q)R$_4$—, —R$_5$[Arg -NH($CH_2$)$_{n5}$CO]$_{n6}$R$_5$—, —R$_5$—[N-guanidino-propyl-Gly]$_{n6}$R$_5$—, in which $n_3$ is an integer number from 0 to 5, $n_4$ is an integer number from 0 to 50, $n_5$ is an integer number from 2 to 6, $n_6$ is an integer number from 2 to 7;

$R_3$ is H or linear or branched $C_1$-$C_4$ alkyl, optionally substituted with —COOH, —CONH$_2$, —NH$_2$ or —OH;

$R_4$ is selected from the group consisting of: —NH—, —CO—, —CONH—, —NHCO—;

$R_5$ is either absent or is the group —R$_4$(Q)R$_4$—;

$R_6$ is H or NH$_2$;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is absent or H or is the following group c(Arg-Gly-Asp-$AA_1$-$AA_2$), in which:

c means cyclic;

$AA_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-$CF_3$-Phe, (D)-4-acetylamine-Phe;

$AA_2$ is selected from the group consisting of: NW—CH[($CH_2$)$_{n7}$—CO]—CO, NW—CH[($CH_2$)$_{n7}$—NH]—CO, NW—[4—($CH_2$)$_{n7}$—CO]-Phe, NW—[4—($CH_2$)$_{n7}$—NH]-Phe, [NW]-Gly, NW-Val, in which W is selected from H, linear or branched $C_1$-$C_6$ alkyl, —($CH_2$)$_{n7}$—COOH where $n_7$ is an integer number from 0 to 5, 4-carboxybenzyl, 4-aminomethylbenzyl;

the $N_1$-oxides, racemic mixtures, its single enantiomers, its single diastereoisomers, the forms E and Z, mixtures thereof, and its pharmaceutically acceptable salts;

carried out according to the following reaction scheme:

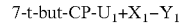

7-t-but-CP-$U_1$+$X_1$-$Y_1$ where 7-t-but-CP represents 7-t-butoxyiminomethylcamptothecin, $U_1$, $X_1$ and $Y_1$ represent respectively the groups U, X and Y as defined above.

8. Process for the preparation of compounds of Formula I

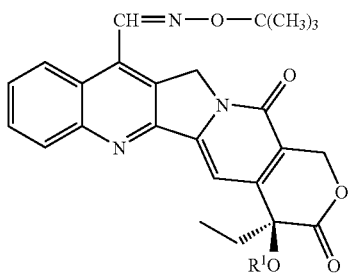

Formula I where:

$R_1$ is the U—X—Y group, in which:

U is one of the following groups —COCHR$_{10}$NH— or CON[($CH_2$)$_{n2}$NHR$_7$]—CH$_2$—, where $R_{10}$ is H or is selected from the group consisting of: linear or branched $C_1$-$C_4$ alkyl, optionally substituted with $C_6$-$C_{14}$ aryl or an amino-alkyl $C_1$-$C_4$; $R_7$ is H or linear or branched $C_1$-$C_4$ alkyl; $n_2$ is an integer number from 2 to 6;

X is H or is a group selected among the following: —COCHR$_3$NH—, —COCHR$_6$($CH_2$)$_{n3}$R$_4$—, —R$_4$—CH$_2$(OCH$_2$CH$_2$)$_{n4}$OCH$_2$R$_4$—, —R$_4$(Q)R$_4$—, —R$_5$[Arg -NH($CH_2$)$_{n5}$CO]$_{n6}$R$_5$—, —R$_5$—[N-guanidino-propyl-Gly]$_{n6}$R$_5$—, in which $n_3$ is an integer number from 0 to 5, $n_4$ is an integer number from 0 to 50, $n_5$ is an integer number from 2 to 6, $n_6$ is an integer number from 2 to 7;

$R_3$ is H or linear or branched $C_1$-$C_4$ alkyl, optionally substituted with —COOH, —CONH$_2$, —NH$_2$ or —OH;

$R_4$ is selected from the group consisting of: —NH—, —CO—, —CONH—, —NHCO—;

$R_5$ is either absent or is the group —$R_4(Q)R_4$—;
$R_6$ is H or $NH_2$;
Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$ -$C_6$), alkylene ($C_1$ -$C_6$)-arylene ($C_6$-$C_{14}$); aromatic or non-aromatic heterocyclyl ($C_3$-$C_{14}$), containing at least one heteroatom selected from the group consisting of O, N, S;
Y is absent or H or is the following group c(Arg-Gly-Asp-$AA_1$-$AA_2$),
in which:
c means cyclic;
$AA_1$ is selected from the group consisting of: (D)-Phe, (D)-Trp, (D)-Tyr, (D)-2- naphthylAla, (D)-4-terbutyl-Phe, (D)-4,4'-biphenyl-Ala, (D)-4-$CF_3$-Phe, (D)-4-acetylamine-Phe;
$AA_2$ is selected from the group consisting of: NW—CH [$(CH_2)_{n7}$—CO]—CO, NW—CH [$(CH_2)_{n7}$—NH]—CO, NW—[4—$(CH_2)_{n7}$—CO]-Phe, NW—[4—$(CH_2)_{n7}$—NH]-Phe, [NW]-Gly, NW-Val, in which W is selected from H, linear or branched $C_1$-$C_6$ alkyl, —$(CH_2)_{n7}$—COOH where $n_7$ is an integer number from 0 to 5, 4-carboxybenzyl, 4-aminomethylbenzyl;
the $N_1$-oxides, racemic mixtures, its single enantiomers, its single diastereoisomers, the forms E and Z, mixtures thereof, and its pharmaceutically acceptable salts; carried out according to the following reaction scheme:

7-t-but-CP-$U_1$–$X_1$+$Y_1$ where 7-t-but-CP represents 7-t-butoxyiminomethylcamptothecin, $U_1$, $X_1$ and $Y_1$ represent respectively the groups U, X and Y as defined above.

9. The compound

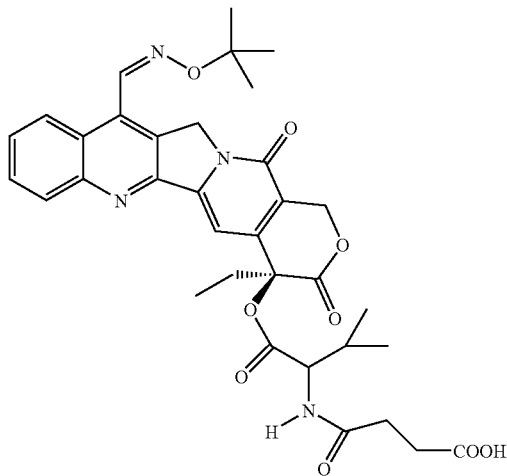

its $N_1$-oxides, racemic mixtures, its single enantiomers, its single diastereoisomers, the forms E and Z, mixtures thereof, its pharmaceutically acceptable salts.

* * * * *